US012599303B2

(12) United States Patent
Miseikis

(10) Patent No.: US 12,599,303 B2
(45) Date of Patent: Apr. 14, 2026

(54) INFORMATION PROCESSING DEVICE, EYESIGHT TEST SYSTEM, INFORMATION PROCESSING METHOD

(71) Applicant: Sony Group Corporation, Tokyo (JP)

(72) Inventor: Justinas Miseikis, Stuttgart (DE)

(73) Assignee: Sony Group Corporation, Tokyo (JP)

( * ) Notice: Subject to any disclaimer, the term of this patent is extended or adjusted under 35 U.S.C. 154(b) by 431 days.

(21) Appl. No.: 18/175,565

(22) Filed: Feb. 28, 2023

(65) Prior Publication Data

US 2023/0284902 A1 Sep. 14, 2023

(30) Foreign Application Priority Data

Mar. 8, 2022 (EP) ..................................... 22160792

(51) Int. Cl.
*A61B 3/14* (2006.01)
*A61B 3/028* (2006.01)
*A61B 3/036* (2006.01)
*G06V 10/82* (2022.01)
*G06V 40/18* (2022.01)

(52) U.S. Cl.
CPC .............. *A61B 3/14* (2013.01); *A61B 3/0285* (2013.01); *A61B 3/036* (2013.01); *G06V 10/82* (2022.01); *G06V 40/18* (2022.01)

(58) Field of Classification Search
CPC ......... A61B 3/14; A61B 3/0285; A61B 3/036; G06V 10/82; G06V 40/18
USPC ....................................................... 351/206
See application file for complete search history.

(56) References Cited

U.S. PATENT DOCUMENTS

| | | | |
|---|---|---|---|
| 10,827,918 B1 | 11/2020 | Nuriel et al. | |
| 2006/0241970 A1* | 10/2006 | Winiarski | A61B 5/486 |
| | | | 705/2 |
| 2017/0188823 A1* | 7/2017 | Ganesan | A61B 3/113 |
| 2018/0125716 A1* | 5/2018 | Cho | G02B 27/0172 |
| 2019/0379869 A1* | 12/2019 | Abou Shousha | G06V 40/193 |
| 2020/0029802 A1 | 1/2020 | Lane et al. | |

(Continued)

OTHER PUBLICATIONS

Aswathi Pacha, "How artificial intelligence can aid eye testing", The Hindu, Sci-Tech, Science, Available Online At: https://www.thehindu.com/sci-tech/science/how-artificial-intelligence-can-aid-eye-testing/article31192456.ece, Mar. 28, 2020, pp. 1-7.

(Continued)

*Primary Examiner* — Sharrief I Broome
(74) *Attorney, Agent, or Firm* — XSENSUS LLP

(57) ABSTRACT

An information processing device for estimating eyesight of a person comprises a processor coupled to memory storing machine readable instructions. The processor obtains image data representing an image of an eye and inputs the data into a machine learning algorithm trained to estimate eyesight characteristics from eye images. The system estimates the person's eyesight by determining at least one of myopia, hyperopia, and astigmatism based on the image data and algorithm output. The invention addresses limitations of traditional manual eyesight tests that are prone to human error and subjective patient feedback. The machine learning algorithm analyzes eye relaxation states and micromovements that indicate optimal vision correction, enabling objective automated eyesight assessment deployable in remote locations or consumer devices.

17 Claims, 3 Drawing Sheets

(56) References Cited

U.S. PATENT DOCUMENTS

| | | | | |
|---|---|---|---|---|
| 2020/0041797 | A1 * | 2/2020 | Samec | A61B 5/14532 |
| 2020/0046222 | A2 * | 2/2020 | Dave | A61B 3/028 |
| 2020/0327304 | A1 * | 10/2020 | Li | G06V 40/19 |
| 2021/0106220 | A1 * | 4/2021 | Abou Shousha | A61B 3/113 |
| 2021/0173206 | A1 * | 6/2021 | Das | G06F 21/32 |
| 2022/0361745 | A1 * | 11/2022 | De Rossi | A61B 3/14 |

OTHER PUBLICATIONS

Jędzierowska et al., "A new method for detecting the outer corneal contour in images from an ultra-fast Scheimpflug camera", BioMedical Engineering OnLine, vol. 18, No. 115, Available Online At: https://biomedical-engineering-online.biomedcentral.com/articles/ 10.1186/s12938-019-0735-1, 2019, pp. 1-22.

Kamiya et al., "Keratoconus detection using deep learning of colour-coded maps with anterior segment optical coherence tomography: a diagnostic accuracy study", BMJ Open, 9:e031313. doi:10. 1136/bmjopen-2019-031313, Available Online At: https://bmjopen. bmj.com/content/9/9/e031313, 2019, pp. 1-7.

Kou et al., "Keratoconus Screening Based on Deep Learning Approach of Corneal Topography", Translational Vision Science & Technology, vol. 9, No. 53, Available Online At: https://tvst. arvojournals.org/article.aspx?articleid=2770836, Sep. 2020, pp. 1-11.

Maureen A. Duffy, "Eye Health: Anatomy of the Eye", VisionAware, Available Online At: https://visionaware.org/your-eye-condition/eye-health/anatomy-of-the-eye/, 2021, pp. 1-5.

Marks et al., "Eyeball squeezing could correct sight", Available Online At: https://www.newscientist.com/article/dn2064-eyeball-squeezing-could-correct-sight/, Mar. 21, 2002, pp. 1-3.

Marina Wang, "Eye, robot: Artificial intelligence dramatically improves accuracy of classic eye exam", Available Online At: https://www.sciencemag.org/news/2020/06/eye-robot-artificial-intelligence-dramatically-improves-accuracy-classic-eye-exam, Jun. 3, 2020, pp. 1-4.

"Your Eye Test", VisionExpress, Available Online At: https://www. visionexpress.com/eye-health/eye-test, 2021, pp. 1-8.

* cited by examiner

100

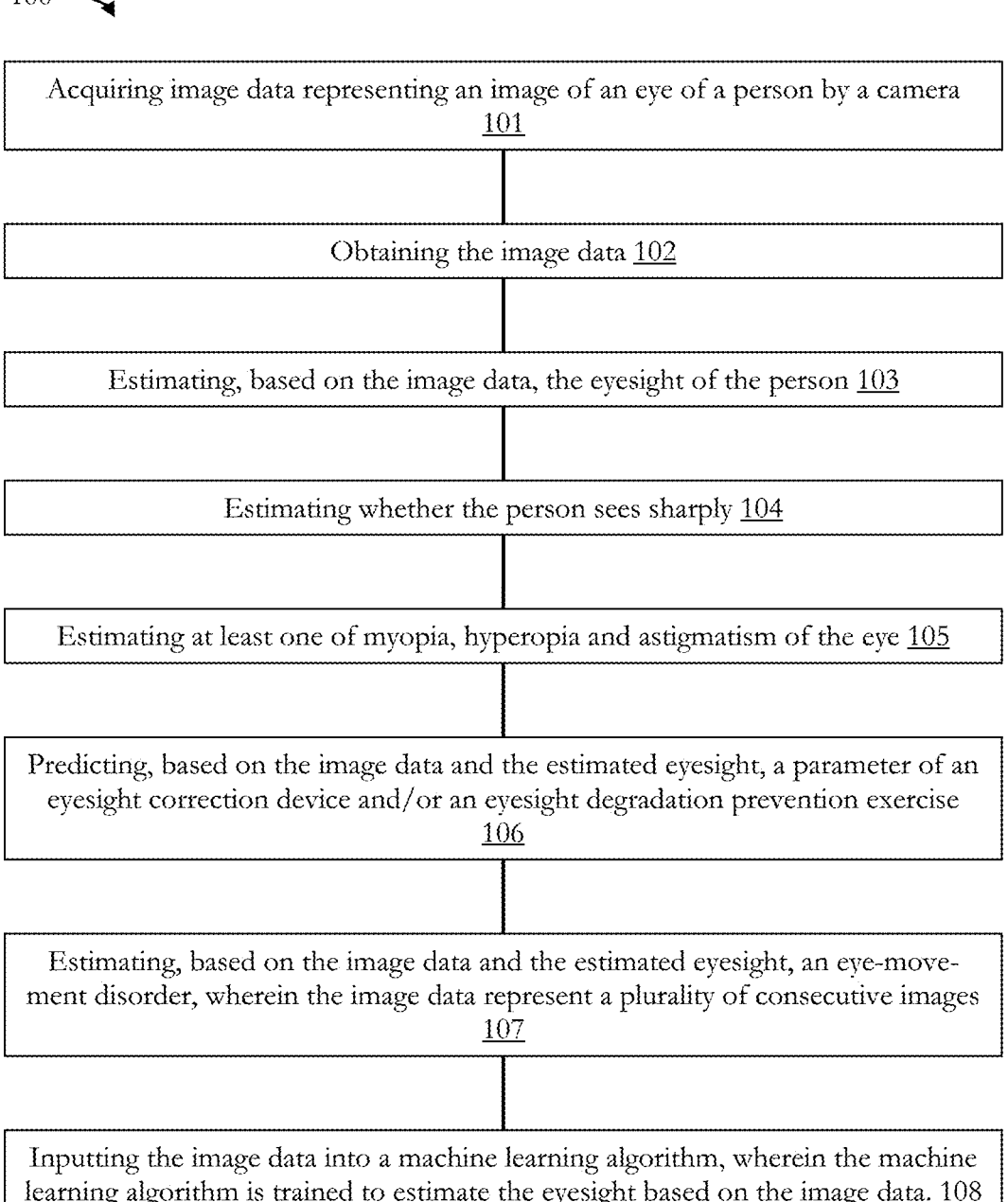

Acquiring image data representing an image of an eye of a person by a camera
101

Obtaining the image data 102

Estimating, based on the image data, the eyesight of the person 103

Estimating whether the person sees sharply 104

Estimating at least one of myopia, hyperopia and astigmatism of the eye 105

Predicting, based on the image data and the estimated eyesight, a parameter of an eyesight correction device and/or an eyesight degradation prevention exercise
106

Estimating, based on the image data and the estimated eyesight, an eye-movement disorder, wherein the image data represent a plurality of consecutive images
107

Inputting the image data into a machine learning algorithm, wherein the machine learning algorithm is trained to estimate the eyesight based on the image data. 108

Fig. 5

INFORMATION PROCESSING DEVICE, EYESIGHT TEST SYSTEM, INFORMATION PROCESSING METHOD

CROSS-REFERENCE TO RELATED APPLICATION

The present application claims priority to European Patent Application No. 22160792.2, filed Mar. 8, 2022, the entire contents of which are incorporated herein by reference.

TECHNICAL FIELD

The present disclosure generally pertains to an information processing device for estimating an eyesight of a person, an information processing method for estimating an eyesight of a person and an eyesight test system.

TECHNICAL BACKGROUND

It is known that the eyesight of a person typically depends on the shape of the cornea which directs the light entering the eye and focuses the rays to hit the retina which is a light-sensitive tissue inside the surface of the eye. The retina contains the photoreceptor cells that convert incoming light into electrical impulses sent to the brain. Inside the retina, there is the macula providing clear central vision. In the center of the macula, there is the fovea which provides the sharpest detail vision.

However, as generally known, if the cornea or lens does not focus strongly enough or the eyeball is too short, the light will focus behind the retina, blurring images of close-up objects. This is known as long-sightedness. Conversely, if the eyeball is too long, the light will focus in front of the retina, yielding the blurry images of far-off objects which is characteristic of short-sightedness.

Current methods for eyesight evaluation are typically based on manual observations and testing by placing various lenses in front of the eye and asking the person under evaluation for the feedback whether the person can see items clearly. However, this method may be prone to human errors either by the patient or the doctor conducting the evaluation, as generally known, which may result in non-ideal selection of lenses, in some cases, thus imperfect vision even with eyesight correcting devices such as glasses or lenses may occur.

Although there exist techniques for eyesight estimation, it is generally desirable to improve the existing techniques.

SUMMARY

According to a first aspect the disclosure provides an information processing device for estimating an eyesight of a person, comprising circuitry configured to:
obtain image data representing an image of an eye of the person; and
estimate, based on the image data, the eyesight of the person.

According to a second aspect the disclosure provides an eyesight test system, comprising:
a lens changing device configured to hold and exchange a lens for testing an eyesight of a person;
a camera configured to acquire image data representing an image of an eye of the person; and
an information processing device for estimating the eyesight of the person, including circuitry configured to:
obtain the image data; and estimate, based on the image data, the eyesight of the person.

According to a third aspect the disclosure provides an information processing method for estimating an eyesight of a person, comprising:
obtaining image data representing an image of an eye of the person; and
estimating, based on the image data, the eyesight of the person.

Further aspects are set forth in the dependent claims, the following description and the drawings.

BRIEF DESCRIPTION OF THE DRAWINGS

Embodiments are explained by way of example with respect to the accompanying drawings, in which:

FIG. 5 schematically illustrates in a flow diagram an embodiment of an information processing method.

DETAILED DESCRIPTION OF EMBODIMENTS

Figure 1:
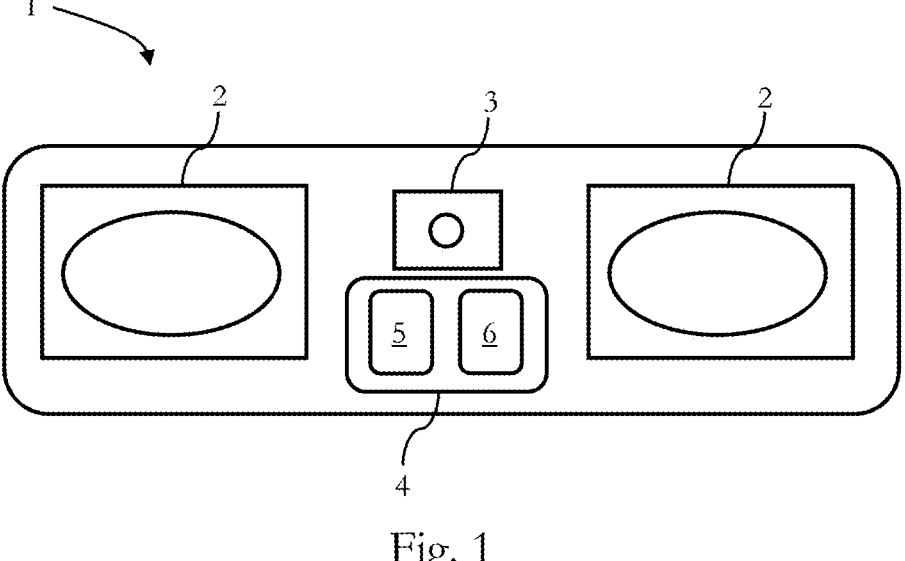
FIG. 1 schematically illustrates in a block diagram an embodiment of an eyesight test system in front view.

Before a detailed description of the embodiments under reference of FIG. 1 is given, general explanations are made.

As mentioned in the outset, it is known that the eyesight of a person typically depends on the shape of the cornea which directs the light entering the eye and focuses the rays to hit the retina which is a light-sensitive tissue inside the surface of the eye. The retina contains the photoreceptor cells that convert incoming light into electrical impulses sent to the brain. Inside the retina, there is the macula providing clear central vision. In the center of the macula, there is the fovea which provides the sharpest detail vision.

However, as generally known, if the cornea or lens does not focus strongly enough or the eyeball is too short, the light will focus behind the retina, blurring images of close-up objects. This is known as long-sightedness. Conversely, if the eyeball is too long, the light will focus in front of the retina, yielding the blurry images of far-off objects which is characteristic of short-sightedness.

As further mentioned in the outset, current methods for eyesight evaluation are typically based on manual observations and testing by placing various lenses in front of the eye and asking the person under evaluation for the feedback whether the person can see items clearly. However, this method may be prone to human errors either by the patient or the doctor conducting the evaluation, as generally known, which may result in non-ideal selection of lenses, in some cases, thus imperfect vision even with eyesight correcting devices such as glasses or lenses may occur.

It is generally known that vision sensors, such as color and DVS ("Dynamic Vision Sensor") cameras (which may be referred to as event camera), are improving in quality and reducing in price, and with a correct lens, they are able to provide high-quality images even at close distances. Deep learning algorithms are known which are able to analyze images and even identify tiny differences in images and classify them accordingly.

It has been recognized that an image of an eye typically includes visual information about a shape of the eyeball and micromovements which are influenced by eye muscle tension and fluid density of the eye. The eye is typically more relaxed when imaging properties of the eye are correct such that a sharp image is obtained on the retina. This may be achieved by eyesight correction devices such as lenses or glasses.

Hence, it has been recognized that an eyesight of a person may be estimated from an image of the eye of the person.

It is envisaged to identify, based on an output of a visual camera (e.g., color, infrared or DVS camera), when an eye of a patient (a person being tested) has the ideal eyesight during an eyesight test.

In some embodiments, different lenses are exchanged in front of the eye(s) observing an image/object typically used in an eyesight test and the camera-based system identifies when the person sees the image/object sharply instead of relying on the feedback of the person being tested.

In some embodiments, a plurality of different lenses is placed consecutively in front of the eye of the person and, when a next lens is placed, a camera captures an image of the eye for estimating an eyesight of the person. In some embodiments, the plurality of lenses has predetermined properties and the information about the lens parameters is used in the estimation of the eyesight of the person.

It has been recognized that such an eyesight test system may provide/achieve at least one of the following: non-biased information, the lens adjustment steps may be finer than in traditional eyesight tests, the eyesight test may be performed faster and automatically, may reduce the likelihood of a human-error and a more personalized eyesight correction.

It is further envisaged to estimate eye conditions such as: myopia, hyperopia, astigmatism.

Moreover, it is envisaged to utilize eye-movement tracking to identify eye-movement disorders such as diplopia, nystagmus.

In some embodiments, the eyesight test system is a suggestive system to the professional who still conducts the exams, uses and verifies the data from the suggestion system. In some embodiments, the eyesight test system provides results in an explainable artificial intelligence manner, for example, text explanation follows indicating why the eyesight test system identified a certain outcome and, thus, the professional who is conducting the exam can easily verify and either accept or decline it.

Moreover, a fully automatic eyesight test system is envisaged which has a small scale factor such that it is easy to transport/ship. Hence, in some embodiments, reliable at-home eyesight test systems for people, e.g., living in remote locations or with limited mobility is provided. This may improve the quality of life for such people by providing them an automatic eyesight test system. Additionally, eyesight correction devices (e.g., lenses, glasses) may be shipped directly to the person who was tested.

Furthermore, in some embodiments, an artificial intelligence ("AI") algorithm is trained predict the vision correction parameters for a person from looking at the eye. In some embodiments, it is not necessary to exchange various corrective lenses in front of the eyes of the person such that the AI algorithm is provided in consumer devices (e.g., a smartphone). In some embodiments, VR/AR ("Virtual Reality/Augmented Reality") glasses (also referred to as smart glasses) may be used as an application. In some embodiments, a mobile phone app is provided and a person holds the mobile phone in front of the face and a camera captures an image for predicting what eyesight correction is needed. In some embodiments, detection of very early changes in the eyesight is facilitated and suggestion prevention exercises or eyesight correction devices are predicted/suggested early on, thus reducing further degradation of the eyesight.

Hence, some embodiments pertain to an information processing device for estimating an eyesight of a person, wherein the information processing device includes circuitry configured to:

obtain image data representing an image of an eye of the person; and estimate, based on the image data, the eyesight of the person.

Some embodiments pertain to an eyesight test system, wherein the eyesight test includes:

a lens changing device configured to hold and exchange a lens for testing an eyesight of a person;

a camera configured to acquire image data representing an image of an eye of the person; and an information processing device for estimating the eyesight of the person, wherein the information processing device includes circuitry configured to:

obtain the image data; and estimate, based on the image data, the eyesight of the person.

In some embodiments, the lens changing device is configured to exchange the lens automatically with a next lens, and wherein the camera is configured to acquire next image data representing a next image after the next lens is placed.

The information processing device may be a mobile device (e.g., a smartphone, a tablet, etc.), smart glasses, an image or video capturing device, a computer, or the like.

The circuitry may be based on or may include or may be implemented by typical electronic components configured to achieve the functionality as described herein.

The circuitry may be based on or may include or may be implemented as integrated circuitry logic and the functionality may be implemented by software executed by a processor or the like. The circuitry may be based on or may include or may be implemented by a CPU (central processing unit), a microcontroller, an FPGA (field programmable gate array), an ASIC (application specific integrated circuit), a GPU (graphical processing unit), a DSP (digital signal processor) or the like.

The circuitry may be based on or may include or may be implemented in parts by typical electronic components and integrated circuitry logic and in parts by software.

The circuitry may include storage capabilities such as magnetic storage, semiconductor storage, etc.

The circuitry may include a data bus for transmitting and receiving data and may implement corresponding communication protocols.

The circuitry may include a display configured to display visual information such as images or videos or text. The circuitry may include a speaker configured to output sound information. The circuitry may include an input interface configured to obtain user input (e.g., via a mouse, via a touch-display, via a keyboard, via a microphone, etc.).

In some embodiments, the information processing device includes a camera configured to acquire the image data.

In some embodiments, the camera is a color camera, or wherein the camera is an infrared camera and the image data are infrared image data, or wherein the camera is an event camera and the image data are event image data.

In some embodiments, the circuitry is configured to input the image data into a machine learning algorithm, wherein the machine learning algorithm is trained to estimate the eyesight based on the image data.

The machine learning algorithm may be an artificial neural network (e.g., a convolutional neural network), a decision tree, a support vector machine or the like.

For training the machine learning algorithm training data is collected, for example, by including a camera into a conventional eyesight test system and images are captured during the conventional eyesight test conducted by a professional and outcomes are marked/labeled. Hence, in some embodiments, automatic labelling of the collected training data is provided and a high diversity of subjects is provided.

In some embodiments, estimating the eyesight includes estimating whether the person sees sharply.

In some embodiments, estimating the eyesight includes estimating at least one of myopia, hyperopia and astigmatism of the eye.

In some embodiments, the circuitry is configured to predict, based on the image data and the estimate eyesight, a parameter of an eyesight correction device.

For example, the machine learning algorithm may output technical design parameters of a lens for glasses or the like.

In some embodiments, the machine learning algorithm is further trained to predict a parameter of an eyesight correction device based on the image data as input.

In some embodiments, the circuitry is configured to predict, based on the image data and the estimated eyesight, an eyesight degradation prevention exercise.

In some embodiments, the image data represent a plurality of consecutive images, and wherein the circuitry is configured to estimate, based on the image data and the estimated eyesight, an eye-movement disorder (e.g., diplopia, nystagmus).

For example, a lens is placed in front of the eye of the person and the plurality of consecutive images is acquired by the camera for tracking an eye-movement.

In some embodiments, the machine learning algorithm is further trained to estimate an eye-movement disorder based on a plurality of consecutive images of an eye of a person.

In some embodiments, the circuitry is configured to output information regarding at least one of an estimation of the eyesight, a parameter of an eyesight correction device, an eyesight degradation prevention exercise and an eye-movement disorder.

As mentioned above, in some embodiments, the eyesight test system is a suggestive system to the professional who still conducts the exams, uses and verifies the data from the suggestion system. In some embodiments, the eyesight test system provides results in an explainable artificial intelligence manner, for example, text explanation follows indicating why the eyesight test system identified a certain outcome and, thus, the professional who is conducting the exam can easily verify and decline it.

Some embodiments pertain to an information processing method for estimating an eyesight of a person, wherein the information processing method includes:

obtaining image data representing an image of an eye of the person; and estimating, based on the image data, the eyesight of the person.

The information processing method may be performed by the information processing device as described herein.

The methods as described herein are also implemented in some embodiments as a computer program causing a computer and/or a processor to perform the method, when being carried out on the computer and/or processor. In some embodiments, also a non-transitory computer-readable recording medium is provided that stores therein a computer program product, which, when executed by a processor, such as the processor described above, causes the methods described herein to be performed.

Returning to FIG. 1, there is schematically illustrated in a block diagram an embodiment of an eyesight test system 1 in front view, which is discussed in the following.

Figure 2:
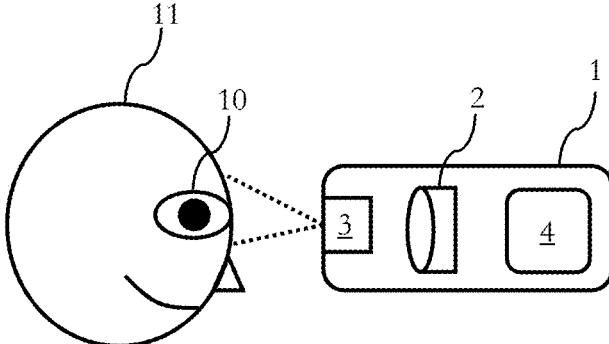
FIG. 2 schematically illustrates an embodiment of an eyesight test system in side view.

The eyesight test system 1 is further discussed under reference of FIG. 2 which schematically illustrates a side view of the eyesight test system 1.

The eyesight test system 1 includes a lens changing device 2, a camera 3 and an information processing device 4.

The lens changing device 2 holds a lens for eyesight testing which can be placed in front of an eye 10 of a person 11.

A professional who conducts the eyesight test on the person 11 may be able to exchange the lens manually with a next lens or the lens may be exchanged automatically.

For example, the lens changing device may include a wheel with a plurality of different (predetermined) lenses which may rotate to place one of the lenses in front of the eye 10 of the person 11.

The camera 3 may be a color camera (e.g., a RGB ("red-green-blue") camera), an infrared camera or an event camera. The camera 3 is configured to acquire image data representing an image of the eye 10 of the person 11.

The information processing device 4 includes a processor 5 and a data storage 6, however, it may further include, e.g., a speaker or a display to output information regarding a result of the eyesight test.

The processor 5 loads a computer-program from the data storage 6 for automatic eyesight testing and executes the computer-program.

The computer-program includes, among other instructions, instructions which cause the processor 5 to instruct the camera 3 to acquire image data and to output the image data, e.g., via a data bus (e.g., a data bus interface in accordance with MIPI ("Mobile Industry Processor Interface Alliance") specifications) to the processor 5.

At first, no lens is placed in front of the person's eye 10 and the processor 5 instructs the camera 3 to acquire first image data representing a first image of the eye 10 which outputs the first image data to the processor 5.

Then, the processor 5 instructs the lens changing device 2 to place a first lens in front of the eye 10 and, in response to completion of placing the first lens, the processor 5 instructs the camera 3 to acquire second image data representing a second image of the eye 10 which outputs the second image data to the processor 5.

Then, the next lens is placed and so on until all of the plurality of different (predetermined) lenses were placed and an image for each of them.

The computer-program further includes instructions which represent an artificial neural network (not shown; "ANN" in the following) for eyesight testing. The ANN may be a convolutional neural network.

The processor 5 thus inputs either the first or the second image data (or third image data etc.) into the ANN when the first or the second image data is obtained. In such embodiments, each image is directly analyzed.

In some embodiments, the processor 5 inputs the first and the second image data (and third image data etc.) into the ANN when all lenses have been placed. In such embodiments, all images are analyzed together.

In some embodiments, two or more images are grouped together, and the groups are processed one after another.

The ANN is trained (training of the ANN will be discussed under reference of FIG. 4) to estimate, based on the image data, the eyesight of the person 11.

The ANN estimates whether the person 11 sees sharply and/or estimates at least one of myopia, hyperopia and astigmatism of the eye 10.

Additionally, the ANN may be trained to predict, based on the image data and the estimated eyesight, a parameter of an eyesight correction device (e.g., a technical design parameter of glasses for the person 11).

Moreover, in some embodiments, the processor 5 instructs the camera 3 to acquire a plurality of consecutive images for each lens for tracking an eye-movement for estimating an eye-movement disorder.

In such embodiments, the ANN is further trained to estimate an eye-movement disorder based on the plurality of consecutive images.

Figure 3:
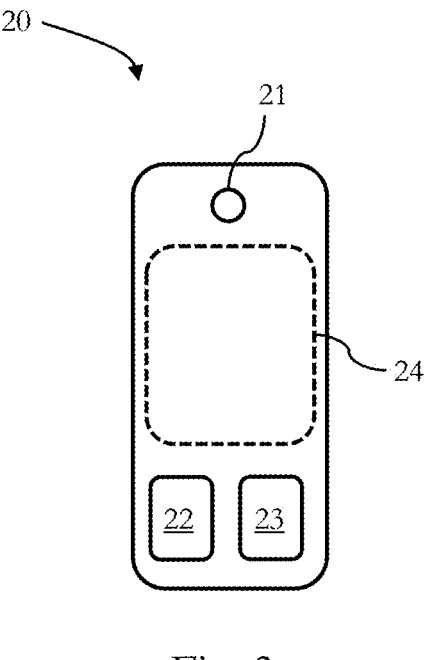
FIG. 3 schematically illustrates in a block diagram an embodiment of an information processing device.

FIG. 3 schematically illustrates in a block diagram an embodiment of an information processing device 20, which is discussed in the following.

The information processing device 20 is a smartphone and includes a camera 21, a processor 22, a data storage 23, and a touch-display 24.

The camera 21 may be a color camera (e.g., a RGB ("red-green-blue") camera), an infrared camera or an event camera.

The person 11 of FIG. 2 may place the smartphone 20 in front of his eyes 10 for estimating an eyesight of his eyes 10. The touch-display 24 may then display information regarding a result of the eyesight test.

The camera 21 is configured to acquire image data representing an image of the eye 10 of the person 11.

The processor 22 loads a computer-program from the data storage 23 for automatic eyesight testing and executes the computer-program.

The computer-program includes, among other instructions, instructions which cause the processor 22 to instruct the camera 21 to acquire image data and to output the image data, e.g., via a data bus (e.g., a data bus interface in accordance with MIPI ("Mobile Industry Processor Interface Alliance") specifications) to the processor 22.

The computer-program further includes instructions which represent an artificial neural network (not shown; "ANN" in the following) for eyesight testing. The ANN may be a convolutional neural network.

The processor 22 inputs the image data into the ANN, wherein the ANN is trained (training of the ANN will be discussed under reference of FIG. 4) to estimate, based on the image data, the eyesight of the person 11.

The ANN estimates whether the person 11 sees sharply and/or estimates at least one of myopia, hyperopia and astigmatism of the eye 10.

Additionally, the ANN may be trained to predict, based on the image data and the estimated eyesight, a parameter of an eyesight correction device (e.g., a technical design parameter of glasses for the person 11).

Moreover, in some embodiments, the processor 22 instructs the camera 21 to acquire a plurality of consecutive images for each lens for tracking an eye-movement for estimating an eye-movement disorder.

In such embodiments, the ANN is further trained to estimate an eye-movement disorder based on the plurality of consecutive images.

Figure 4:
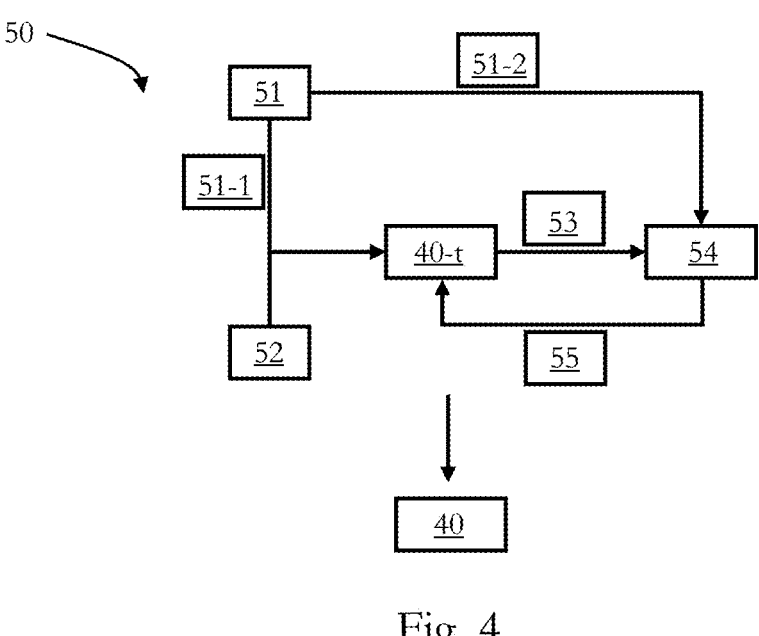
FIG. 4 schematically illustrates in a block diagram an embodiment of a training method of an artificial neural network for estimating an eyesight of a person.

FIG. 4 schematically illustrates in a block diagram an embodiment of a training method 50 of an artificial neural network 40-t for estimating an eyesight of a person, which is discussed in the following.

In the beginning of the training method 50, the ANN 40 as discussed under reference of FIGS. 1, 2 and 3 is in a training stage 40-t.

The training method 50 is based on ground-truth image data 51, in particular, the ground-truth image data 51 include a plurality of image data acquired with a camera, wherein each image data 51-1 of the plurality of image data represent an image of an eye of a person. A plurality of different eyes with various eyesight are covered in the ground-truth image data 51. Moreover, a plurality of different lenses in front of the eyes are covered in the ground-truth image data 51.

Each image data 51-1 of the plurality of image data in the ground-truth image data 51 are associated with a label 51-2 representing an estimation of the eyesight of the person. In particular, the label 51-2 includes an indicator which indicates whether the person sees sharply, and which indicates at least one of myopia, hyperopia and astigmatism of the eye.

Optionally, the training method 50 is further based on ground-truth lens parameters 52 which indicate a technical design parameter of the lens (as a parameter of an eyesight correction device) used in the corresponding image data 51-1. In such embodiments, the ANN may include one or more additional layers to predict also a parameter of an eyesight correction device based on the image data and the estimated eyesight of the person.

The following describes the training for one image and associated lens parameters which is then repeated for the other images.

The image data 51-1 and, optionally, the associated lens parameters 52 are input into in the neural network 40-t in the training stage.

The neural network 40-t in the training stage generates a classification result 53, wherein the classification result 53 is an estimation of the eyesight of the person and, optionally (when lens parameters 52 are used), a prediction of a parameter of an eyesight correction device.

The prediction of the parameter of the eyesight correction device represents a prediction of a parameter of an eyesight correction device which is likely to improve the eyesight of the person (and, thus, it does not correspond to a prediction of the lens parameter 52).

A loss function 54 generates, based on a difference between the label 51-2 and the classification result 53, weight updates 55 for the neural network 40-t in the training stage.

The process is repeated until all images and, optionally, associated lens parameters 52 are processed.

Then, at the end of the training method 50, the weights are obtained and, thus, the ANN 40 is obtained.

FIG. 5 schematically illustrates in a flow diagram an embodiment of an information processing method 100.

The information processing method 100 may be performed by the information processing device as discussed herein.

At 101, image data representing an image of an eye of a person is acquired by a camera, as discussed herein.

At 102, the image data is obtained, as discussed herein.

At 103, based on the image data, the eyesight of the person is estimated, as discussed herein.

At 104, it is estimated whether the person sees sharply, as discussed herein.

At 105, at least one of myopia, hyperopia and astigmatism of the eye is estimated, as discussed herein.

At 106, based on the image data and the estimated eyesight, a parameter of an eyesight correction device and/or an eyesight degradation prevention exercise is predicted, as discussed herein.

At 107, based on the image data and the estimated eyesight, an eye-movement disorder is estimated, wherein the image data represent a plurality of consecutive images, as discussed herein.

At 108, the image data is input into a machine learning algorithm, wherein the machine learning algorithm is trained to estimate the eyesight based on the image data, as discussed herein.

It should be recognized that the embodiments describe methods with an exemplary ordering of method steps. The specific ordering of method steps is however given for illustrative purposes only and should not be construed as binding.

All units and entities described in this specification and claimed in the appended claims can, if not stated otherwise, be implemented as integrated circuit logic, for example on a chip, and functionality provided by such units and entities can, if not stated otherwise, be implemented by software.

In so far as the embodiments of the disclosure described above are implemented, at least in part, using software-controlled data processing apparatus, it will be appreciated that a computer program providing such software control and a transmission, storage or other medium by which such a computer program is provided are envisaged as aspects of the present disclosure.

Note that the present technology can also be configured as described below.

(1) An information processing device for estimating an eyesight of a person, including circuitry configured to:
  obtain image data representing an image of an eye of the person; and
  estimate, based on the image data, the eyesight of the person.

(2) The information processing device of (1), wherein estimating the eyesight includes estimating whether the person sees sharply.

(3) The information processing device of (1) or (2), wherein estimating the eyesight includes estimating at least one of myopia, hyperopia and astigmatism of the eye.

(4) The information processing device of anyone of (1) to (3), wherein the circuitry is configured to predict, based on the image data and the estimate eyesight, a parameter of an eyesight correction device.

(5) The information processing device of anyone of (1) to (4), wherein the circuitry is configured to predict, based on the image data and the estimated eyesight, an eyesight degradation prevention exercise.

(6) The information processing device of (1) to (5), wherein the image data represent a plurality of consecutive images, and wherein the circuitry is configured to estimate, based on the image data and the estimated eyesight, an eye-movement disorder.

(7) The information processing device of anyone of (1) to (6), wherein the circuitry is configured to output information regarding at least one of an estimation of the eyesight, a parameter of an eyesight correction device, an eyesight degradation prevention exercise and an eye-movement disorder.

(8) The information processing device of anyone of (1) to (7), wherein the circuitry is configured to input the image data into a machine learning algorithm, wherein the machine learning algorithm is trained to estimate the eyesight based on the image data.

(9) The information processing device of anyone of (1) to (8), including a camera configured to acquire the image data.

(10) The information processing device of (9), wherein the camera is a color camera, or wherein the camera is an infrared camera and the image data are infrared image data, or wherein the camera is an event camera and the image data are event image data.

(11) The information processing device of anyone of (1) to (10), wherein the information processing device is a mobile device, or wherein the information processing device is smart glasses.

(12) An eyesight test system, including:
  a lens changing device configured to hold and exchange a lens for testing an eyesight of a person;
  a camera configured to acquire image data representing an image of an eye of the person; and
  an information processing device for estimating the eyesight of the person, including circuitry configured to:
    obtain the image data; and
    estimate, based on the image data, the eyesight of the person.

(13) The eyesight test system of (12), wherein the lens changing device is configured to exchange the lens automatically with a next lens, and wherein the camera is configured to acquire next image data representing a next image after the next lens is placed.

(14) An information processing method for estimating an eyesight of a person, including:
  obtaining image data representing an image of an eye of the person; and
  estimating, based on the image data, the eyesight of the person.

(15) The information processing method of (14), wherein estimating the eyesight includes estimating whether the person sees sharply.

(16) The information processing method of (14) or (15), wherein estimating the eyesight includes estimating at least one of myopia, hyperopia and astigmatism of the eye.

(17) The information processing method of anyone of (14) to (16), including predicting, based on the image data and the estimate eyesight, a parameter of an eyesight correction device and/or an eyesight degradation prevention exercise.

(18) The information processing method of anyone of (14) to (17), wherein the image data represent a plurality of consecutive images, comprising estimating, based on the image data and the estimated eyesight, an eye-movement disorder.

(19) The information processing method of (14) to (18), including inputting the image data into a machine learning algorithm, wherein the machine learning algorithm is trained to estimate the eyesight based on the image data.

(20) The information processing method of (14) to (19), including acquiring the image data by a camera.

(21) A computer program comprising program code causing a computer to perform the method according to anyone of (14) to (20), when being carried out on a computer.

(22) A non-transitory computer-readable recording medium that stores therein a computer program product, which, when executed by a processor, causes the method according to anyone of (14) to (20) to be performed.

The invention claimed is:

1. An information processing device for estimating an eyesight of a person, comprising:
  a processor coupled to a memory that stores machine readable instructions thereon which, when executed by the processor, causes the processor to obtain image data representing an image of an eye of the person;

input the image data into a machine learning algorithm trained to estimate eyesight characteristics from eye images based on visual features of the eye including at least one of eyeball shape and eye micromovements; and estimate, based on the image data and an output of the machine learning algorithm, the eyesight of the person by determining at least one of myopia, hyperopia, and astigmatism of the eye.

2. The information processing device according to claim 1, wherein estimating the eyesight includes estimating whether the person sees sharply.

3. The information processing device according to claim 1, wherein the circuitry is configured to predict, based on the image data and the estimate eyesight, a parameter of an eyesight correction device.

4. The information processing device according to claim 1, wherein the circuitry is configured to predict, based on the image data and the estimated eyesight, an eyesight degradation prevention exercise.

5. The information processing device according to claim 1, wherein the image data represent a plurality of consecutive images, and wherein the circuitry is configured to estimate, based on the image data and the estimated eyesight, an eye-movement disorder.

6. The information processing device according to claim 1, wherein the circuitry is configured to output information regarding at least one of an estimation of the eyesight, a parameter of an eyesight correction device, an eyesight degradation prevention exercise and an eye-movement disorder.

7. The information processing device according to claim 1, comprising a camera configured to acquire the image data.

8. The information processing device according to claim 7, wherein the camera is a color camera, or wherein the camera is an infrared camera and the image data are infrared image data, or wherein the camera is an event camera and the image data are event image data.

9. The information processing device according to claim 1, wherein the information processing device is a mobile device, or wherein the information processing device is smart glasses.

10. An eyesight test system, comprising:

a lens changing device configured to hold and exchange a lens for testing an eyesight of a person; and a camera configured to acquire image data representing an image of an eye of the person;

an information processing device for estimating the eyesight of the person, including a processor coupled to a memory that stores machine readable instructions thereon which, when executed by the processor, causes the processor to obtain image data representing an image of an eye of the person;

input the image data into a machine learning algorithm trained to estimate eyesight characteristics from eye images based on visual features of the eye including at least one of eyeball shape and eye micromovements; and estimate, based on the image data and an output of the machine learning algorithm, the eyesight of the person by determining at least one of myopia, hyperopia, and astigmatism of the eye.

11. The eyesight test system according to claim 10, wherein the lens changing device is configured to exchange the lens automatically with a next lens, and wherein the camera is configured to acquire next image data representing a next image after the next lens is placed.

12. An information processing method for estimating an eyesight of a person, comprising:

obtaining image data representing an image of an eye of the person;

inputting the image data into a machine learning algorithm trained to estimate eyesight characteristics from eye images based on visual features of the eye including at least one of eyeball shape and eye micromovements; and estimating, based on the image data and an output of the machine learning algorithm, the eyesight of the person by determining at least one of myopia, hyperopia, and astigmatism of the eye.

13. The information processing method according to claim 12, wherein estimating the eyesight includes estimating whether a sharp image is obtained on the person's retina.

14. The information processing method according to claim 12, comprising predicting, based on the image data and the estimate eyesight, a parameter of an eyesight correction device and/or an eyesight degradation prevention exercise.

15. The information processing method according to claim 12, wherein the image data represent a plurality of consecutive images, comprising estimating, based on the image data and the estimated eyesight, an eye-movement disorder.

16. The information processing method according to claim 12, comprising acquiring the image data by a camera.

17. The information processing device of claim 1, wherein the machine learning algorithm is an artificial neural network, wherein the artificial neural network is a convolutional neural network, a decision tree, or a support vector machine.

* * * * *